United States Patent
De Graaff et al.

(10) Patent No.: US 9,345,686 B2
(45) Date of Patent: May 24, 2016

(54) MACROCYCLIC LACTONE DRUG DELIVERY SYSTEM

(75) Inventors: Wouter De Graaff, Oss (NL); Raymond Zeeman, Oss (NL); Niels Honcoop, Oss (NL)

(73) Assignee: Intervet Inc., Madison, NJ (US)

( * ) Notice: Subject to any disclaimer, the term of this patent is extended or adjusted under 35 U.S.C. 154(b) by 216 days.

(21) Appl. No.: 13/256,264

(22) PCT Filed: Mar. 16, 2010

(86) PCT No.: PCT/EP2010/053339
§ 371 (c)(1),
(2), (4) Date: Nov. 18, 2011

(87) PCT Pub. No.: WO2010/106046
PCT Pub. Date: Sep. 23, 2010

(65) Prior Publication Data
US 2012/0052108 A1    Mar. 1, 2012

Related U.S. Application Data

(60) Provisional application No. 61/160,942, filed on Mar. 17, 2009.

(30) Foreign Application Priority Data

Mar. 17, 2009  (EP) ................................. 09155383

(51) Int. Cl.
| *A61K 31/35* | (2006.01) |
| *A61K 31/365* | (2006.01) |
| *A61K 9/00* | (2006.01) |
| *A61K 9/20* | (2006.01) |
| *A61K 9/24* | (2006.01) |

(52) U.S. Cl.
CPC ............. *A61K 31/365* (2013.01); *A61K 9/0024* (2013.01); *A61K 9/209* (2013.01); *A61K 9/2027* (2013.01)

(58) Field of Classification Search
CPC ........................... A61K 31/365; A61K 9/0024
See application file for complete search history.

(56) References Cited

U.S. PATENT DOCUMENTS

| 4,144,317 A | 3/1979 | Higuchi et al. | |
| 2004/0247634 A1* | 12/2004 | Martinod et al. | 424/405 |
| 2005/0063907 A1* | 3/2005 | Brandon et al. | 424/9.4 |
| 2007/0141102 A1* | 6/2007 | De Graaff et al. | 424/423 |

FOREIGN PATENT DOCUMENTS

| BR | PI 0504244-5 | | 9/2007 | |
| BR | PI 0504244-5 A | | 9/2007 | |
| WO | 03/002102 A1 | | 1/2003 | |
| WO | WO 03/004059 | | 1/2003 | |
| WO | WO 03/051335 | * | 6/2003 | ............... A61K 9/12 |

OTHER PUBLICATIONS

International Search Report corresponding to PCT/EP2010/053339, mailed May 6, 2010.
Bawa, et al., "An Explanation for the Controlled Release of Macromolecules from Polymers", Journal of Controlled Release, 1985, pp. 259-267, vol. 1.
Langer, R., "New Methods of Drug Delivery", Science, 1990, pp. 1527-1533, vol. 249.
Maeda, et al., "Design of controlled-release formulation for ivermectin using silicone", International Journal of Pharmaceutics, 2003, pp. 9-19, vol. 261.
European Search Report for EP Application No. EP 09 15 5383, dated Oct. 2, 2009.

* cited by examiner

*Primary Examiner* — Brian Gulledge

(57) ABSTRACT

Disclosed is a drug delivery system from which a macrocyclic lactone can be released with a desirable zero order release profile. The system is based on the use of thermoplastic polymers, and particularly of polyethylene vinyl acetate copolymers (EVA). The drug delivery system of the invention comprises a solid non-porous reservoir in which the macrocyclic lactone is contained, preferably in a concentration well above the saturation concentration, and a non-porous skin covering the reservoir not initially loaded with the drug. The system is preferably in the form of a rod, wherein the core and the skin are concentric, and the end surfaces of the rod are not skin-covered.

16 Claims, 8 Drawing Sheets

Figure 14: Mean ivermectin plasma concentrations [ng/mL plasma] (approximately 84 mg ivermectin/dog)
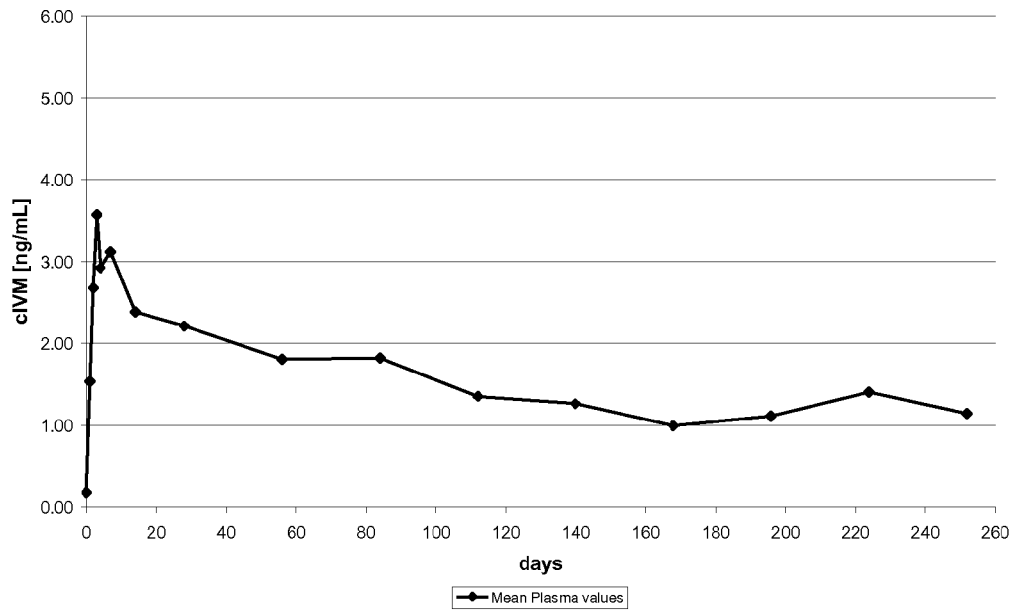
Figure 15 : Mean ivermectin plasma concentrations [ng/mL plasma] (approximately 84 mg ivermectin/dog)
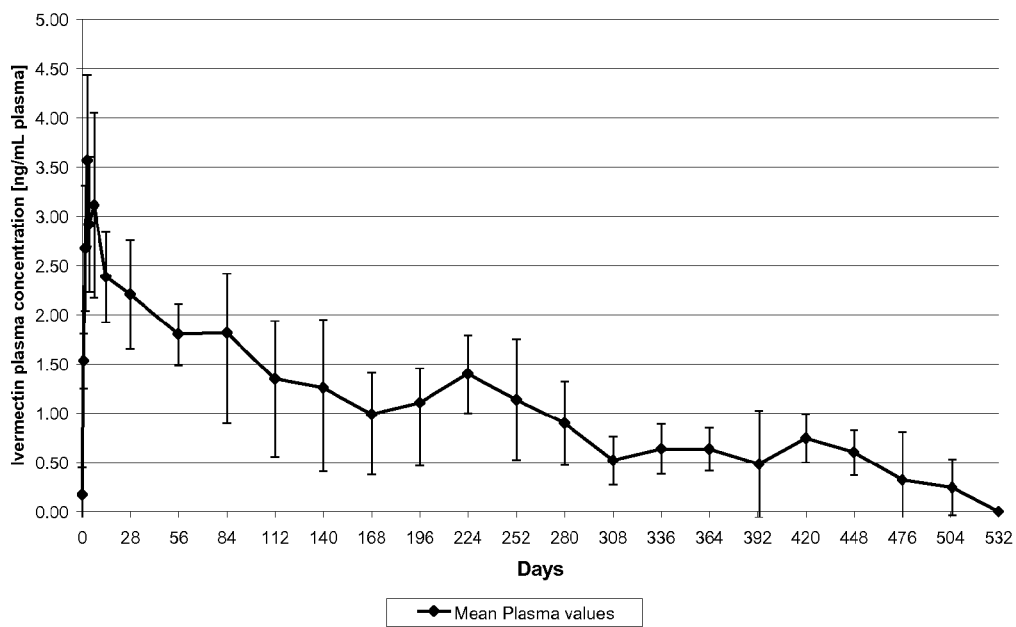

MACROCYCLIC LACTONE DRUG DELIVERY SYSTEM

RELATED APPLICATIONS

This application is a national stage entry under 35 U.S.C. §371 of PCT/EP2010/053339 filed on Mar. 16 2010 which claims priority to U.S. Provisional Application No. 61/160,942 filed on Mar. 17, 2009 and to EP Application No. 09155383.4 filed on Mar. 17, 2009.

FIELD OF THE INVENTION

The invention pertains to a drug delivery system, particularly an implant, for the controlled release of a macrocyclic lactone as an active ingredient to animals. The invention also pertains to uses of such drug delivery systems and to methods of making them.

BACKGROUND OF THE INVENTION

The macrocyclic lactones, i.e. the avermectin and milbemycin series of compounds are potent endo- and ectoparasitic agents. The compounds which belong to this series are either natural products or are semi-synthetic derivatives thereof. The structure of these two series of compounds are closely related and they both share a complex 1,6-membered macrocyclic lactone ring; the avermectins comprise a disaccharide substituent in the 1,3-position of the lactone ring, which the milbemycins do not.

Macrocyclic lactones, e.g. ivermectin are commonly used in the veterinary science as an anti-parasitic medication. It is effective against most common intestinal worms, most mites and some lice.

To this end, it is desired to provide macrocyclic lactones in a drug delivery system that is capable of the controlled release of the active compound, preferably yielding a constant release for a prolonged period of time.

As is recognized in the art, a constant release is difficult to achieve. Most, if not all, controlled release systems will have an initially high release (burst release). The release thereafter, in a curve of release versus time, will usually show a certain degree of decline, varying from a steep linear curve (first order release) to the more desirable flat curve of near zero order release. A challenging objective is to obtain zero order release (i.e. a truly flat curve of release against time).

A reference on ivermectin implants is Maeda H., et al., "Design of controlled-release formulation for ivermectin using silicon," *Int. Journal of Pharmaceutics*, 261, pp. 9-19 (2003). This reference discusses a cylindrical implant having a drug-loaded silicone matrix coated with an impermeable lateral coating (i.e., a coating everywhere except the ends). This "covered-rod" type of implant design allows drug release to occur only at the uncovered ends of the structure. The reference compares this design with a design in which the silicone core matrix is not laterally covered by an impermeable coating. It is concluded that the release from the latter implant (which can be described as "matrix release") is first order release.

The thrust of the article is to show that the "covered rod" design is capable of approaching zero order release. However, additional measures are needed to obtain sufficient release. E.g., in order to have a near zero order release for a period of 2-3 months, it is necessary to add polyethylene glycol. Without such an additive, it can be inferred from the paper that the release is at an insufficient level.

The need to use an additive generally is a disadvantage. E.g. evidence of the additive's safety will need to be provided. Particularly for the preferred PEPPG this might require extensive toxicological investigations with an unknown outcome. Another serious drawback of substantial amounts of additives in that this will result in less space in the implant to accommodate active ingredients. For implants it is of essential importance to use high drug loads in order to retain acceptable implant dimensions. In the event that a substantial amount of the composition is made up of inactive additives this will result in larger implant dimensions.

To the person skilled in the art, it is further recognizable as a drawback if the release characteristics are dependent on the inclusion of additives, rather than on the choice of implant carrier material. This complicates the manufacturing process, and it goes against a general desire to keep the number of additives low. Furthermore, the need for additives that affect release, leads to a lower degree of freedom to include other additives (that may be needed for other purposes), as in such a system any change in the composition goes with the risk of deteriorating the release characteristics.

In the case of drug-loaded implants this e.g. means that one has a lower degree of freedom to include useful additives such as radiocontrast agents. The latter, e.g. barium sulfate, are important tools to locate an implant in events where its quick removal is required. This is of recognized importance for drug delivery systems that provide prolonged release. E.g. if an animal experiences an adverse event as a result of taking a single dosage of an immediate-release drug, the administration of the drug can simply be discontinued. If, however, these circumstances take place in the case of an implant, providing prolonged release, it will be necessary to remove the implant. For this purpose, it is important that the implant can be located in the body. To this end X-ray is the most suitable technique. This requires X-ray visibility of the drug delivery system, which is attained by the inclusion of a radiocontrast agent. Further, drug delivery systems such as disclosed by Maeda et al. in which the release characteristics are dependent on a structure of pores or channels, and in which the release has to be tuned by means of additives, are relatively complicated from a process and design point of view. The covered rod as disclosed in Maeda et al is basically a matrix containing water soluble drug(s) and optionally also water soluble excipients. This matrix is covered by a water impermeable skin. The mechanism of release is the ingress of water via the open terminal ends and the drug is slowly released in a near zero order fashion only via the terminal ends. As a result of water ingress and the dissolution of water soluble material an open porous channel structure is formed. The purpose of the water impermeable skin is to prevent release via the lateral side.

The present invention is a drug delivery system of the reservoir type. The reservoir is essentially non-porous and drug release is not driven by the ingress of water into the system. Instead the release mechanism is based on diffusion of drug molecules through a non-porous polymer medium. In the interior of the dosage form e.g. the implant—contrary to a covered rod design—water does not play a role in the diffusion process. Hence dissolution via the open ends is only marginally contributes to the steady state release of the system and release predominantly takes place via the lateral rate controlling skin.

The big advantage is that the release is proportional to the surface area of the lateral side and hence for a chosen diameter to the length of the implant.

Moreover, in Maeda et al, zero order release kinetics is not observed in vivo.

It would be desired to provide a drug delivery system for the controlled release of a macrocyclic lactone that is capable of releasing the macrocyclic lactone for an extended period of time, and preferably at a constant level of release. It would also be desired to provide a drug delivery system for the controlled release of a macrocyclic lactone that can be manufactured in a simple, straightforward process. It would further be desired to provide a drug delivery system for the controlled release of a macrocyclic lactone that has a good tolerance for the inclusion of additives, and that particularly allows the inclusion of a radiocontrast agent.

Another drawback of the "covered rod" type of implant is that it is essentially not protected against dose-dumping. This refers to the untimely, and unwanted, release of large amounts of the dose contained in the implant, if it is damaged before or upon insertion. Thus, e.g. cutting a covered rod into two pieces will inevitably result in doubling of the release as well as early depletion. The latter is particularly disturbing while unanticipated early depletion will leave the implant carrying animal unprotected. The reservoir type implant according to the invention is substantially resistant against dose dumping. Cutting the implant in half does not substantially affect the release rate. While in case of the covered rod design—realising that release is proportional surface area exposed to the watery environment e.g. body fluids—damage to the skin will immediately result in a largely increased release rate.

Based on the teaching of Maeda et al., the person skilled in the art will have difficulty finding a system that addresses the foregoing desires. For, the authors teach that for ivermectin a new method of release control is necessary, as compared to matrix release of proteins. This is consistent with other authors. E.g. a further background to drug delivery systems for controlled release can be found in a paper by Rajan Bawa et al., Journal of Controlled Release 1 1985 p 259-265. With reference to release systems based on biocompatible polymers such as ethylene-vinyl acetate copolymer, it is indicated that these polymers are impermeable to molecules larger than 600 Da (g/mole). It is further described that in these cases release can be obtained, provided that a tortuous, interconnected pore network be formed. This is well-recognized by specialists in the field, as is apparent from another background reference, "New methods of Drug Delivery", Robert Langer, Science, 249 (4976) 1990, 1527-1533. This author confirms that drugs to be released need to have a molecular weight below 600, and supports that large molecules can be released via the formation of a porous path.

Based on the foregoing, the person skilled in the art faces difficulty when addressing the controlled release of macrocyclic lactones, which have molecular weights above the critical upper limit of 600. E.g. moxidectin has a molecular weigh of about 640 g/mole and ivermectin is as high as 875 g/mol.

As a further background on attempts to provide macrocyclic lactone implants, reference is made to BR PI0504244. This document describes, in general terms, subcutaneous implants of ethylene vinyl acetate and polydimethyl siloxane (silicone). The implant essentially is made by first mixing the active ingredient with silica, and then with the polymer or silicone. Although the document does not provide enough detail to enable actually making an implant based on the described technology, it is clear that the active ingredient is not taken up into a continuous polymeric matrix, but in a system having a silica phase. The silica should be expected to serve the creation of a network of interconnecting particles, as the percolation threshold (the point at which particle interconnection will occur) typically is low for high surface area materials such as silica's. This effectively generates a porous path through the matrix, and this too speaks against release from the macrocyclic lactone through the polymer itself.

Another reference is WO 03/002102. This document relates to silastic-based mini implants for the sustained release of active substances. In recognizing the aforementioned danger of dose-dumping, the document provides a more ore less mechanical solution. Rather than seeking formulation technology to help in preventing dose-dumping, the document describes a sustained release apparatus including a plurality of mini-implants or pellets. Thus, the aforementioned danger is contained by the sheer small size of the individual implants. This is practically cumbersome, and far from the ideal of a single implant with a long duration of action. The mini implants are disclosed for a great many active compounds.

Yet another desire, not satisfied in the art, is to provide a drug delivery system, preferably an implant that allows an extended release, of one year or more, of the macrocyclic lactone compound and preferably of at least 1.5 to 3 years. Particularly, it is desired to provide such an extended release drug delivery system that, during the aforementioned periods of use, exhibits near zero order release.

SUMMARY OF THE INVENTION

In order to better address one or more of the foregoing desires, the invention, in one aspect, is a drug delivery system for the controlled release of a macrocyclic lactone as an active ingredient, comprising a solid non-porous reservoir made of a pharmaceutically acceptable, non-degradable thermoplastic polymer, preferably a polyethylene vinyl acetate copolymer, loaded with the macrocyclic lactone and a non-porous skin covering the reservoir, the skin comprising a thermoplastic polymer, preferably a polyethylene vinyl acetate copolymer, in which the macrocyclic lactone is present.

Another aspect is a drug delivery system for the controlled release of a macrocyclic lactone as an active ingredient, comprising a solid non-porous reservoir made of a pharmaceutically acceptable polyethylene vinyl acetate copolymer, loaded with the macrocyclic lactone and a non-porous skin covering the reservoir, the skin comprising a polyethylene vinyl acetate copolymer wherein the macrocyclic lactone is released substantially by diffusion through the skin of the drug delivery system.

Another aspect is a drug delivery system as described above, in the form of a cylindrical rod wherein the reservoir and the skin layer are concentric with the axis of the rod.

The invention, in another aspect, is a drug delivery system for the controlled release of a macrocyclic lactone as an active ingredient, obtainable by a method in which a thermoplastic polymer, preferably a polyethylene vinyl acetate copolymer core loaded with the macrocyclic lactone, is co-extruded with a thermoplastic polymer, preferably a polyethylene vinyl acetate copolymer not loaded with the macrocyclic lactone, and the resulting co-extrudate is cut, wherein the direction of cutting is substantially different from the direction of extruding, and preferably perpendicular thereto.

In a further aspect, the invention resides in uses of the drug delivery system as an antiparasitic implant, and related methods of treatment, i.e. a method of treating parasitic diseases in animals, which method includes administering to an animal the drug delivery system as described above, comprising an antiparasitically effective amount of a macrocyclic lactone.

In yet another aspect, the invention provides a drug delivery system for the controlled release of a macrocyclic lactone, having a near zero order release profile and does not allow dose dumping as defined below.

BRIEF DESCRIPTION OF THE DRAWINGS

FIG. 14 shows the in vivo plasma levels of ivermectin in dogs until day 260

FIG. 15 shows the in vivo plasma levels of ivermectin in dogs until day 532

DETAILED DESCRIPTION OF THE INVENTION

Figure 1A:
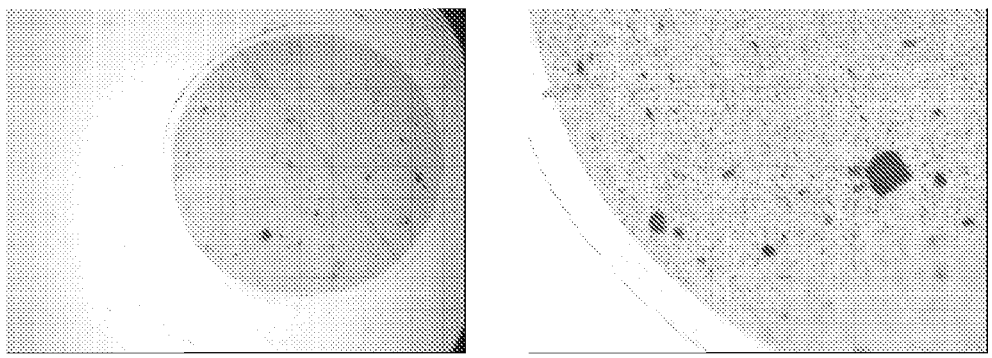
FIGS. 1A and 1B show a cross section of a bi-layered fiber of variant A (loaded with ivermectin) and E (loaded with moxidectin)

In a broad sense, the invention is based on the unexpected discovery that, provided a judicious design for the drug delivery system is chosen, macrocyclic lactones, despite their relatively high molecular weights, can be released from a non-porous reservoir system using thermoplastic co-polymers. Particularly, the invention is based on the unexpected discovery that thermoplastic polymers, particularly ethylene vinyl acetate copolymers, are capable of providing a diffusion-limited release of macrocyclic lactones through a non-porous polymer medium, despite their relatively high molecular weights.

This brings about several benefits. Thus, an easy and straightforward tuning of the release-rate can be done by varying skin thickness and/or ethylene vinyl acetate copolymer grade. The drug delivery systems of the invention can be manufactured in an economically attractive and straightforward manufacturing process using co-extrusion technology. Near zero order release kinetics are attainable. The system has a good robustness against dose dumping (i.e. the unwanted, untimely release of a high amount of drug), has a low residual content, (i.e. high amounts of the active ingredient are released from the system and only a relatively low amount (typically between 10-30 wt %) is not released and remains in the delivery system as residual amount) and provides the possibility to formulate a long acting system (e.g. 1-3 years).

The aforementioned design involves a solid, non-porous reservoir wherein the active ingredient is present, preferably in a concentration above the saturation concentration at 25° C. More preferably, the concentration is well above the saturation concentration, so as to ensure a sufficiently large reservoir of undissolved active compound so as to ensure a continuous supplementation of released amounts of active compound.

The design further involves a non-porous skin, which is believed to act as a rate-controlling membrane. Upon manufacture of the drug delivery device, the skin is preferably not loaded with the active compound. It will be appreciated by the skilled person that, directly after manufacture (i.e. as soon as contact exists between the drug-loaded solid reservoir and the preferably unloaded skin), drug compound can diffuse into the skin, dissolving therein until the dissolved compound has reached the equilibrium concentration. It is not excluded, although not desired either, that the skin is made of a material loaded with active compound ab initio, as long as the concentration is below the saturation concentration.

The reservoir and the skin are essentially non-porous. The term "non-porous" refers to an effective porosity of close to zero. This should be understood as being as low a porosity as possible with due regard to the form of the drug delivery system. E.g. at the lateral end of a rod, not covered by a skin, a few active substance pockets will be connected directly to the environment and therewith the effective porosity is not exactly zero. Thus, also in an essentially non-porous system one cannot exclude that a minor percentage of active substance could be exposed and would therewith behave locally as if the reservoir were porous. In an effectively non-porous reservoir the amount of drug substance loaded that would be accessible through open pores is less than 10 wt. % and likely lower, preferably less than 5 wt. % and more preferably less than 2 wt. %.

Thus, the release of the macrocyclic lactone is not triggered by the presence of porous channels, through which the drug will migrate, but is fully based on diffusion through the thermoplastic material itself.

In the drug delivery system of the invention, the skin covers the solid reservoir. In a most straightforward form, this means that the skin forms the entire outer surface of the drug delivery device, i.e. not leaving any part of the solid reservoir in an exposed state. This is advantageous in the sense that it would avoid any burst release as a result of a lack of exposed parts of the solid reservoir. However, such a system is more expensive from a manufacturing point of view.

A much preferred way of producing a drug delivery system having a solid reservoir and a skin, involves co-extrusion. Herein concentric streams of solid reservoir material and skin material are extruded through a coaxial nozzle, resulting in a thread-like material having the solid reservoir material at the inside, thus forming a core, and the skin material surrounding the core. From the normally continuous co-extrudate output, individual drug delivery systems can be provided by simply cutting the co-extrudate at desired lengths. The cutting will be done in a direction substantially different from the direction of extruding (i.e. so as to avoid splicing the extrudate parallel to the virtual axis thereof), and preferably perpendicular thereto (resulting in cylindrical rods wherein the core and the skin are concentric with the axis of the rod).

It will be understood that, although a cylindrical rod is a preferred shape, the drug delivery device of the invention can also have another shape, e.g. bar shapes, hexagonal rods, etc.

In the co-extruded cylindrical rod as described above, the cut ends on either side will expose a surface area of the core. At the beginning of use, this will result in an onset of action (the burst phase) from these open ends. But, after that, drug release predominantly takes place through the skin (in the case of a co-extrudate, the implant's lateral wall).

The mechanism of drug release is diffusion-driven permeation through the dense, non-porous polymer solid reservoir and rate-controlling membrane. Release is nearly zero-order. The release is tailored by, for example, adjusting skin thickness, EVA composition in the solid reservoir and/or rate-controlling membrane, and drug load. Formation of an open porous channel-like structure facilitating drug release generally does not occur.

The term 'solid reservoir' refers to the inner part of the drug delivery system, the outer part being the skin. It is conceivable that the drug delivery system of the invention comprises more parts than a single solid reservoir and a skin. E.g., the system may comprise multiple concentric layers. This can involve an intermediate layer between the solid reservoir and the skin. This can also involve a solid reservoir in the form of an intermediate layer loaded with the drug, and a core that is not loaded.

The macrocyclic lactone is loaded into the solid reservoir at a concentration preferably greater than saturation (i.e., at a level well above the solubility of the drug in the thermoplastic polymer), and is thus present in the polymer partially in the solid state and partially in the dissolved state. The initial concentration of the macrocyclic lactone in the solid reservoir will generally be of from 5%, preferably of from 10%, and more preferably of from 20% by weight, to 60%, preferably 50% by weight. This concentration, however, may vary, with a further preferred range being of from 25% to 50% by weight.

The macrocyclic lactones (avermectins and milbemycins) are products, or chemical derivatives thereof, of soil microorganisms belonging to the genus *Streptomyces*.

In a preferred embodiment of the invention, the macrocyclic lactones e.g. avermectins, milbemycins and derivatives thereof are selected from the group which includes but is not limited to, abamectin, doramectin, emamectin, eprinomectin, ivermectin, and selamectin (avermectin and derivatives thereof), milbemycin D, milbemycin oxime, lepimectin, and moxidectin (milbemycin and derivatives thereof) and mixtures thereof.

One particularly contemplated macrocyclic lactone parasiticide is ivermectin. Ivermectin is a semi-synthetic derivative of avermectin, and is generally produced as a mixture of at least 80% 22,23-dihydroavermectin $B1_a$ and less than 20% 22,23-dihydroavermectin $B1_b$. Ivermectin is disclosed in U.S. Pat. No. 4,199,569. Ivermectin has been used as an antiparasitic agent to treat various parasitic diseases since the mid-1980's. An alternative particularly contemplated macrocyclic lactone parasiticide is moxidectin.

Other macrocyclic lactone parasiticides include, for example the following:

Abamectin This compound is, for example, identified as avermectin $B1_a/B1_b$ in U.S. Pat. No. 4,310,519. Abamectin contains at least 80% of avermectin $B1_a$, and not more than 20% of avermectin $B1_b$.

Doramectin This compound is known as 25-cyclohexyl-avermectin $B_1$. Its structure and preparation are discussed in, for example, U.S. Pat. No. 5,089,480.

Emamectin This compound also is known as 4"-deoxy-4"-epi-methylaminoavermectin $B_1$. Its preparation is discussed in, for example, U.S. Pat. Nos. 5,288,710 and 5,399,717.

Eprinomectin This compound is known as 4"-epi-acetylamino-4"-deoxy-avermectin $B_1$. It was developed for use in all cattle classes and age groups.

Selamectin This compound also is known as 25-cyclohexyl-25-de(1-methylpropyl)-5-deoxy-22,23-dihydro-5-(hydroxyimino)-avermectin B1 monosaccharide.

Milbemycin and milbemycin oxime This compound also is known as B41. It is isolated from the fermentation broth of a Milbemycin-producing strain of *Streptomyces*. The microorganism, fermentation conditions, and isolation procedures are discussed in, for example, U.S. Pat. Nos. 3,950,360 and 3,984,564. Moxidectin This compound is discussed in, for example, U.S. Pat. No. 4,916,154.

Lepimectin This is a chemically modified milbemycin macrolide (6R,13R,25R)-5-O-demethyl-28-deoxy-6,28-epoxy-13-[(Z)-[(methoxyimino)phenylacetyl]oxy]-25-methylmilbemycin B mixture with (6R,13R,25R)-5-O-demethyl-28-deoxy-6,28-epoxy-25-ethyl-13-[(Z)-[(methoxyimino) phenylacetyl]oxy]milbemycin B.

A radio contrast agent, preferably barium sulfate may be added to the implant (e.g., the core) to make the implant X-Ray-visible. The barium sulfate, when present, will be present in the core material at a concentration of 4-30 wt %, preferably 6-20 wt %, and more preferably 8-15 wt %. It is important to note that the BaSO4 is dispersed in a continuous polymer medium and therefore is retained in the implant. For safety reasons, this is of essential importance. E.g. a covered rod may be less suitable. The leaching process will make the implant porous and hence it might easily loose the Xray absorbing particles.

The pharmaceutically acceptable, non-biodegradable, thermoplastic polymer that can be used in practising the invention may in principle be any thermoplastic polymer or elastomer material that is suitable for pharmaceutical use. The latter refers, initial to biocompatibility and to a processing temperature that should not be too high, in order to avoid adverse impact, such as degradation or conversion, of active substances. The processing temperature, i.e. at which the polymer can be extruded, is preferably below 140° C. Suitable polymers include poly ethylene vinyl acetate, polyethylene methyl acrylate, polyethylene butyl acrylate, poly (ether) urethanes, and styrene-butadiene-styrene copolymers.

In a preferred embodiment, ethylene-vinylacetate copolymer (poly-EVA) is used due to its excellent mechanical and physical properties (e.g. solubility of the active substance in the material and its relatively low processing temperature).

The solid reservoir and the rate-controlling skin are preferably both made of polyethylene vinyl acetate co-polymers ("EVA"). Grades of these polymers are normally characterized with reference to the weight percentage of vinyl acetate. Thus "EVA-28" has a vinyl acetate content of about 28% by weight.

The EVA used in the reservoir preferably comprises of from 15-40% by weight of vinyl acetate, preferably of from 25 to 35% by weight, and most preferably it is EVA-28. The vinyl acetate in the rate-controlling skin will be about 7-35% by weight, preferably of from 15 to 30% by weight. Most preferably, also the skin comprises EVA-28.

The poly-EVA can be any commercially available ethylene-vinyl acetate copolymer, such as the products available under the trade names: Elvax, Evatane, Lupolen, Movriton, Ultrathene, Ateva and Vestypar.

The drug delivery system of the invention can be manufactured by methods known in the art of polymer processing. Generally this will involve heating the polymer for the reservoir before dissolving the avermectin compound therein, e.g. using a blend extruder. The preferred method of obtaining, is a simple and straightforward process, the preferred coaxial structure having the reservoir as a rod-shaped core, and the skin laterally circumfering this, is co-extrusion.

The co-extrusion can be done e.g. using a set-up consisting of a skin extruder that processes a thermoplastic granulate used for the skin, and a core extruder that processes the granulate used for the reservoir, as delivered by a blend extruder in which the macrocyclic lactone and, optionally, also the radiocontrast agent, are taken up into the polymer. The melt flows are typically combined in a spinneret having concentric apertures, resulting in a skin-core fiber.

The person skilled in the art knows how to set processing parameters such as flow rate (which can be controlled by a set of separate spinning pumps). Another parameter is the extrusion temperature (in the case of EVA e.g. 80° C. to 140° C., and preferably 90° C.-120° C. and the extrusion rate, e.g. of from 1 to 5 m/min.

Extrusion leads to a co-axial fiber, with a large degree of freedom as to fiber diameter. For the implants of the invention, the diameter generally ranges from 0.5 mm to 5 mm. A preferred range is 1 mm to 4 mm, more preferably 1.5 mm to 3 mm, and most preferably 1.5 mm to 2.5 mm. and a skin thickness of from 20 to 160 µm, and preferably of from 25 to 165 µm. The resulting thread is cooled down to room temperature (e.g. using a water bath), dried (e.g. on air) and stored (e.g. wound on a reel) or further processed (e.g. cut into rods, e.g. of 2 to 10 cm, preferably 4 to 8 cm and most preferably about 6 cm.

The drug delivery system of the invention can be used as an antiparasitic medicament in animals, especially in non-human animals. Antiparasitic medicament means a medicament for treating parasitic infections including parasitoses of an animal.

The term "(parasitic) infection" includes conditions associated with or caused by one or more (parasitic) pathogens, said conditions include clinical conditions and non-clinical conditions such as conditions not directly leading to clinical symptoms in the infected animal but leading to economic losses. Such economic losses can be e.g. by depression of growth in young animals, lower feed efficiency, lower weight gain in meat producing animals, lower milk production in ruminants, lower egg production in laying hens, or lower wool-production in sheep. The treatment of infection generally implies the suppression of parasite (e.g. helminth) burdens in the animal below that level at which economic loss occurs.

The term "parasitoses" includes clinically manifest conditions and diseases associated with or caused by one or more parasites directly, such as, for example parasitic gastroenteritis or anemia in ruminants e.g. sheep and goats or colic in horses.

The phrase "treatment of infections including parasitoses" means to partially or completely inhibit the development of infections or parasitoses of an animal susceptible to infection or parasitoses, prevent, reduce or completely eliminate the symptoms of infections or parasitoses of an animal having infections or parasitoses, and/or partially or completely cure infections or parasitoses of an animal having infections or parasitoses.

The preferred use is to prevent and treat larval heartworm (i.e., microfilariae) infections, particularly in canines and felines.

Heartworm infection is caused by a filarial organism *Dirofilaria immitis Dirofilaria immitis* is often referred to as the canine heartworm but can also infect cats and ferrets. At least 70 species of mosquitoes can serve as intermediate hosts; *Aedes, Anopheles*, and *Culex* are the most common genera acting as vectors. Heartworm disease has been reported in most countries with temperate, semitropical, or tropical climates, including the USA, Canada, and southern Europe. In companion animals, infection risk is greatest in dogs and cats housed outdoors.

As for most parasites, the life cycle of *Dirofilaria immitis*, the helminth that causes heartworm, includes a variety of life forms. Adult forms of the parasite are quite large and preferentially inhabit the heart and pulmonary arteries of an animal. Males worms are typically about 12 cm (centimeters) to about 20 cm long and about 0.7 mm to about 0.9 mm wide; female worms are about 25 cm to about 31 cm long and about 1.0 to about 1.3 mm wide. Sexually mature adults, after mating, produce microfilariae which are only about 300 µm (micrometers) long and about 7 µm wide. The microfilariae traverse capillary beds and circulate in the vascular system of the dog in concentrations of about $10^3$ to about $10^5$ microfilariae per ml of blood. If the dog is maintained in an insect-free environment, the life cycle of the parasite cannot progress. However, when microfilariae are ingested by the female mosquito during blood feeding on an infected dog, subsequent development of the microfilariae into larvae occurs in the mosquito. The microfilariae go through two larval stages (L1 and L2) and finally become mature third stage larvae (L3) of about 1.1 mm length, which can then be transmitted back to the dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood.

The macrocyclic lactones ivermectin, milbemycin oxime, moxidectin, and selamectin are currently used in heartworm prevention. Ivermectin is the most commonly used heartworm preventative drug in companion animals, and is generally considered safe at recommended dosage levels. If these are exceeded, side effects such as tremors, staggering, dilated pupils, loss of body weight, or death may occur. As a consequence of normal dosing regimes for ivermectin, the treated animals necessarily receive a relatively large quantity of the drug which is to remain effective for an extended period. This in turn means that shortly after treatment the animal has a very high concentration of ivermectin in its bloodstream, with this concentration tailing off during the remainder of the period. This is to be contrasted with a more preferable treatment protocol wherein a substantially constant level of ivermectin is maintained on a continuing basis.

The drug delivery device according to the current invention can be administered as an implant. However, alternative administration forms, such as e.g. intravaginal devices or intra-ruminal boluses in ruminants are contemplated. Several modified-release delivery systems have been developed, that take advantage of the unique anatomy of the ruminant forestomach, i.e. for intra-ruminal administration. An intra-ruminal bolus is a specific formulation for ruminants (cattle, sheep, goats, buffalos, camelids, deer etc). It is a veterinary delayed release delivery system which remains in the rumeno-reticular sac of a ruminant animal over an extended period of time and in which the therapeutically active substance has a predictable and delayed release pattern. Such intra-ruminal boluses are usually administered using a balling gun or another suitable device.

Preferably the implant is administered subcutaneously. A suitable administration site is in small animals like dogs or other canine animals and cats or other feline animals is e.g. the umbilical area or the neck. In other animals different implantation sites can be used, e.g. the ear or the ear ground. The implant is inserted with a suitable insertion device that is known in the art.

The drug delivery systems according to this invention are useful in treating parasitic infections such as parasitic helminth or insect or acarid infections of animals. A "parasitically effective amount," is the amount or quantity of the macrocyclic lactone compound that is required to alleviate or reduce parasite numbers in or on an animal, and/or to inhibit the development of infections such as parasite infections in or on an animal, in whole or in part. Factors affecting the preferred dosage may include, for example, the parasite species infection to be treated and the development stages of the parasites, the type (e.g., species and breed), age, size, sex, diet, activity, and condition of the of the infected animal; the administration route; pharmacological considerations, such as the activity, efficacy, pharmacokinetic, and toxicology profiles of the particular composition administered; and whether the compound according to this invention being administered as part of a combination of active ingredients. Thus, the preferred amount of the macrocyclic lactone compound can vary, and, therefore, can deviate from the typical dosages set forth below. Determining such dosage adjustments is generally within the skill of those in the art.

With reference to the preferred compounds (ivermectin and moxidectin), the preferred choice of thermoplastic polymer (EVA) and the preferred shape of the system (a coaxial rod) the invention provides for an implant capable of delivery of a macrocyclic lactone (particularly ivermectin) at an effective dose (e.g., 2-3 µg/kg animal per day) for 1-3 years. In some embodiments, this implant can be used to deliver a higher dose of a macrocyclic lactone (particularly ivermectin), e.g., 10-50 µg/kg animal per day) for 1 year.

The invention also provides a drug delivery system for the controlled release of a macrocyclic lactone, having a release profile qualifying as near zero order or zero order release.

Zero order release and near zero order release are terms known to the skilled person. According to the invention, zero order release refers to an in vitro release rate of 1 in accordance with either or both of the below methods. Near zero order deviates from the outcome of 1, generally by less than 25% and preferably by less than 10%.

In the first method, the semi-empirical equation of Peppas (Pharm. Acta Helv 60, Nr 4 (1985)) is applied on the in-vitro release data $$\frac{Mt}{M\infty} = k * t^n$$

With: $Mt/M\infty$=fractional release of the drug, k=constant, t=release time

If the value "n" approaches 1.0 this indicates a non-Fickian release mechanism (zero order release kinetics).

In the second method, the in-vitro release during the final 10% of the release period is divided by the average in-vitro release rate for the release period after initial burst release. If the ratio is 1.0, a perfect zero-order release kinetics is obtained.

With in vitro release taken as a reliable model, the drug delivery devices of the invention enable an in vivo release profile (after initial burst release) preferably for a period of at least 100 days, and more preferably for a period of one year or more. Serum levels obtained with implants according to the object invention show a surprisingly flat development of in vivo levels. The on-set levels are only about 50% higher than the semi-steady state levels and this implant does show near zero order release kinetics. This brings about a considerable advantage in view of the limited therapeutic window of macrocyclic lactones, and particularly the preferred drug ivermectin, in canines and felines. In effect, the near zero order release characteristics o of the drug delivery system of the invention render it exceptionally suitable for use in canines and felines.

In another embodiment a drug delivery system for release of macrocyclic lactones is provided comprising at least one compartment, which comprises (i) a drug-loaded non-biodegradable thermoplastic polymer core layer, (ii) a drug-loaded non-biodegradable thermoplastic polymer intermediate layer and (iii) a non-medicated non-biodegradable thermoplastic polymer skin covering the intermediate layer, wherein said core layer is loaded with a first compound, in particular a antiparasitic compound, and wherein said intermediate layer is loaded with a second compound, in particular a antiparasitic compound.

At least one of the pharmaceutically active compounds is a macrocyclic lactone. The second pharmaceutically active compound can be another macrocyclic lactone or another drug, especially an antiparasitic compound.

In one embodiment the core layer forms the core of the drug delivery system. In an alternative embodiment, the drug delivery system comprises an additional non-medicated core that is covered by the core layer.

The drug delivery system according to the invention may also comprise more layers than the core, intermediate and skin layers mentioned above. The layers form a tri- or multi-axial fiber that is used for shaping a delivery system.

This drug delivery system of the invention is preferably a single compartment system, which means that the whole system consists of the same segment that is made of the same type of drug loaded reservoir e.g. a fiber. The fiber can consist of three, four or more layers, of which at least two layers are loaded with an active ingredient.

The invention will be illustrated with reference to the following, non-limiting examples and the accompanying non-limiting Figures.

Example I

An implant is prepared by a co-extrusion process exemplified as follows:

A. Formation of Pre-Mix

Dry powder mixing is performed with the macrocyclic lactone; EVA 28 powder (ethylene vinyl acetate copolymer containing 28% by weight vinyl acetate); and, optionally, barium sulphate. The macrocyclic lactone is mixed with the EVA 28 powder in a stainless steel drum using a Rhonrad (Barrel-hoop principle) with a fixed rotation speed of approximately 47 rpm for 60 min.

B. Extrusion of the Medicated Core

The homogenized powder pre-mix is blend-extruded using a 25 mm, co-rotating, double-screw, blend extruder. The resulting polymer strands are cut into granules using a granulator. Afterward, the granules are lubricated with 0.1 wt % magnesium stearate to facilitate co-extrusion. Example compositions of such resulting granules are as follows (all compositions are given in weight percent):

TABLE 1

Example Granule Compositions

| Material | Example 1 | Example 2 | Example 3 |
|---|---|---|---|
| Ivermectin | 10 | 50 | — |
| Barium sulphate | 3 | 3 | 3 |
| Moxidectin | — | — | 25 |
| EVA 28 | 86.9 | 46.9 | 71.9 |
| Magnesium stearate | 0.1 | 0.1 | 0.1 |

C. Co-Extrusion

A Fourne co extruder (18/15 mm screws) is used for co-extrusion of the 2-layer fiber. Although the co extruder has 3 extruders, only two are used in this process. The 18 mm extruder processes the core material, while the 15 mm extruder processes the skin layer. The two extruders are connected with a 2-compartment spinning block with 2 separate spinning pumps. These pumps are used to accurately control the volume flow rate of the polymer melts. The thicknesses of both layers can be adjusted by controlling volume flow rates. The 2-polymer melt flows are combined in the spinneret to form a 2-layered fiber. The target fiber diameter is 2.5 mm. All co-axial fibers are extruded at 85-105° C. at a speed of 1.5 m/min. Examples of prepared fibers are summarized in the following table:

TABLE 2

Example Fiber Dimensions/Compositions

| Variant | Target skin thickness [μm] | Skin material | Core batch (from Table 1) | Target Fiber diameter [mm] |
|---|---|---|---|---|
| A1 | 90 | EVA 28 | Example 2 | 2.5 |
| A2 | 90 | EVA 28 | Example 1 | 2.5 |
| A3 | 90 | EVA 33* | Example 1 | 2.5 |
| B1 | 30 | EVA 28 | Example 2 | 2.5 |
| B2 | 30 | EVA 15** | Example 2 | 2.5 |
| C1 | 150 | EVA 33 | Example 2 | 2.5 |
| C2 | 150 | EVA 15 | Example 2 | 2.5 |
| D1 | — | — | Example 2 | 2.5 |
| E1 | 90 | EVA 15 | Example 3 | 2.5 |
| E2 | 90 | EVA 33 | Example 3 | 2.5 |
| E3 | 90 | EVA 28 | Example 3 | 2.5 |
| F1 | 30 | EVA 33 | Example 3 | 2.5 |
| F2 | 30 | EVA 28 | Example 3 | 2.5 |
| G1 | — | — | Example 3 | 2.5 |

*EVA 33 is ethylene vinylacetate copolymer containing 33% vinyl acetate.
**EVA 15 is ethylene vinylacetate copolymer containing 15% vinyl acetate.

Figure 1B:
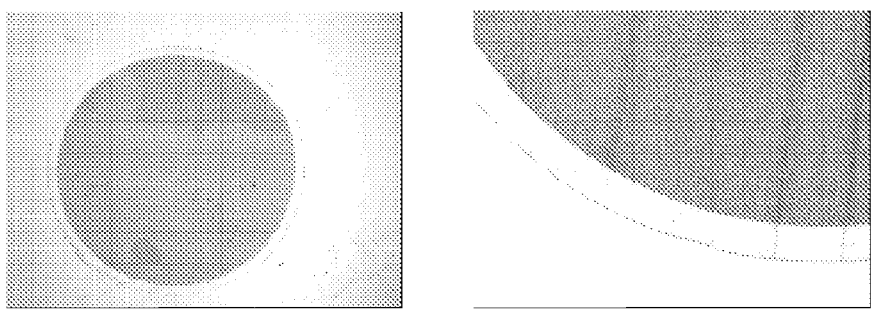

Photographs of typical examples of bi-layered cross-sections of variants A (loaded with Ivermectin) and E (loaded with Moxidectin) are provided in FIG. 1A and FIG. 1B, respectively.

D. Cutting

After extrusion, the collected bi-layer fiber is manually cut into implants of 6 cm. The implants are stored in closed containers at 2-8° C.

E. In-Vitro Release Rates at 37° C. in 0.9% SLS in Water

Figure 2:
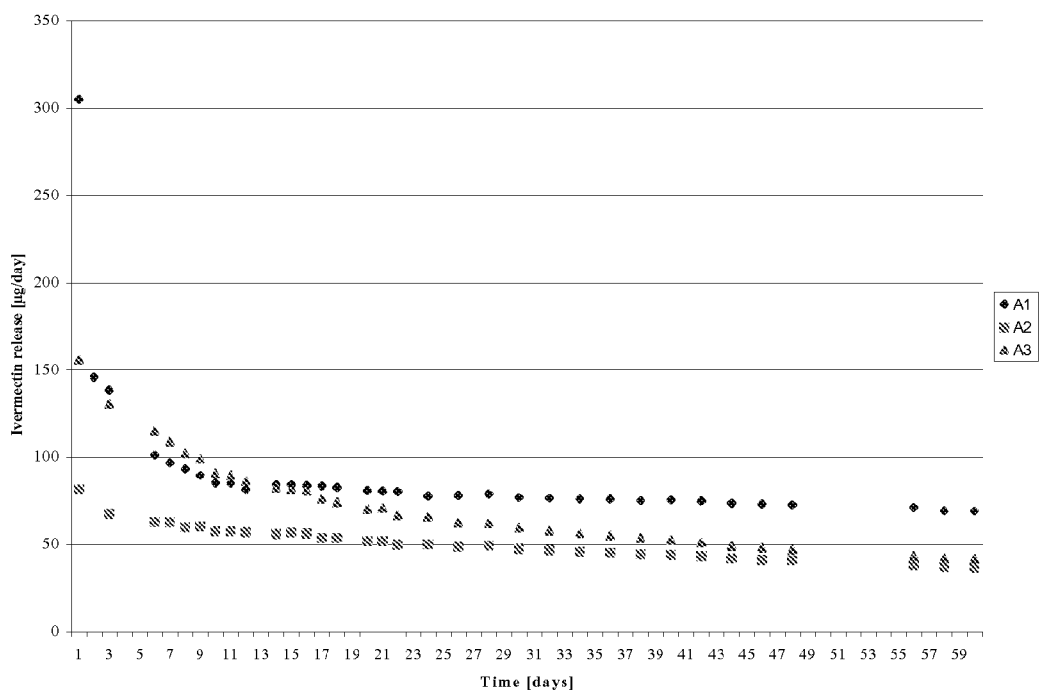
FIG. 2 shows the in vitro ivermectin release of implant designs of variant A
Figure 3:
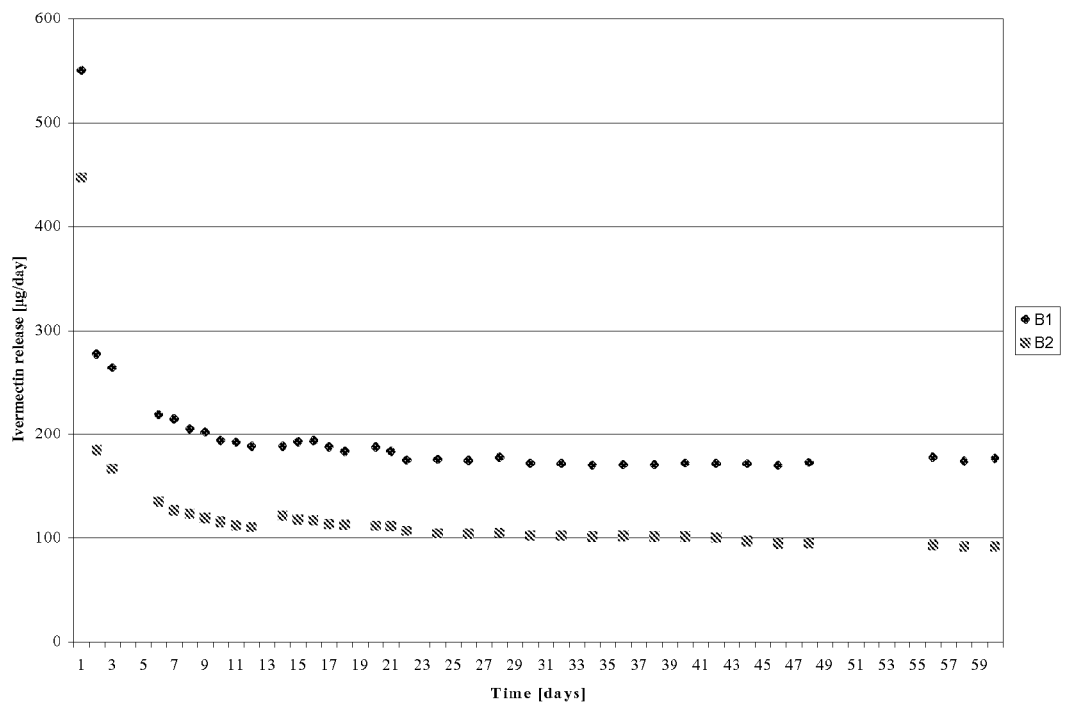
FIG. 3 shows the in vitro ivermectin release of implant designs of variant B
Figure 4:
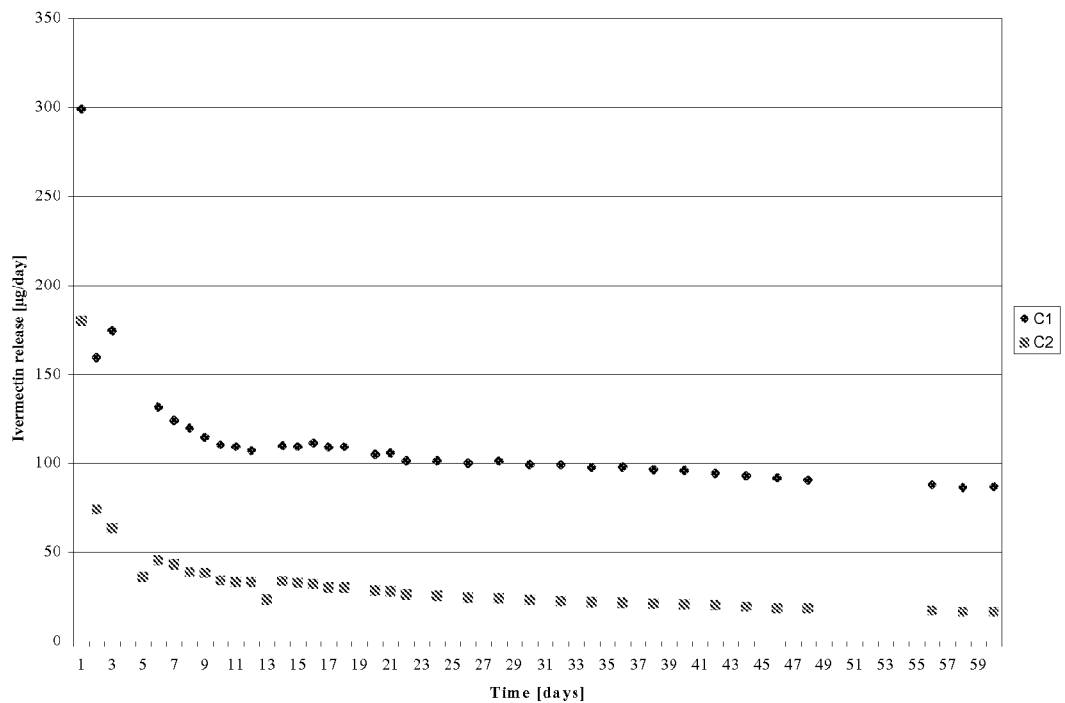
FIG. 4 shows the in vitro ivermectin release of implant designs of variant C
Figure 5:
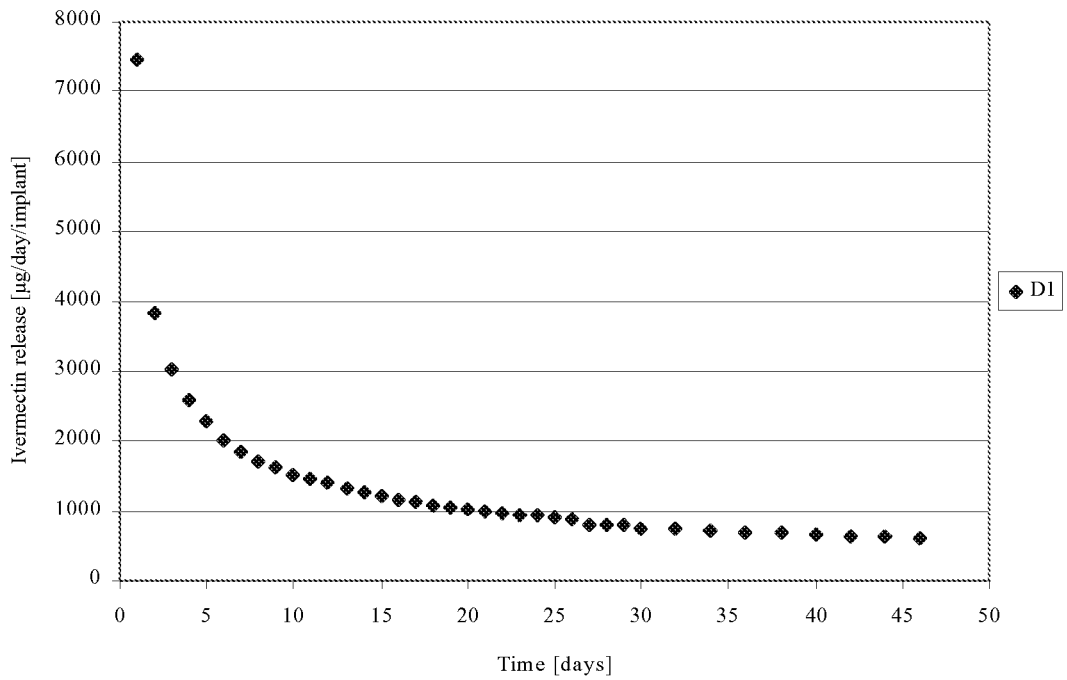
FIG. 5 shows the in vitro ivermectin release of implant designs of variant D

Results for in-vitro release for implants containing ivermectin are shown in Table 3A. FIG. 2 shows the in-vitro release profiles of implant designs of variant A. FIG. 3 shows the in-vitro release profiles of implant designs of variant B. FIG. 4 shows the in-vitro release profiles of implant designs of variant C. FIG. 5 shows the in-vitro release profiles of implant designs of variant D.

TABLE 3A

In-vitro Ivermectin release rates in water/sodium lauryl sulphate (SLS) (0.9%).

| Variant | Ivermectin release day 1 [μg/day] | Ivermectin release day 2-60 [μg/day] | Ivermectin release day 60 [μg/day] |
|---|---|---|---|
| A1 | 305 | 79 | 69 |
| A2 | 82 | 47 | 37 |
| A3 | 156 | 62 | 42 |
| B1 | 551 | 184 | 177 |
| B2 | 448 | 106 | 82 |
| C1 | 299 | 101 | 87 |
| C2 | 180 | 26 | 17 |
| D1 | 7441 | ongoing | ongoing |

Figure 6:
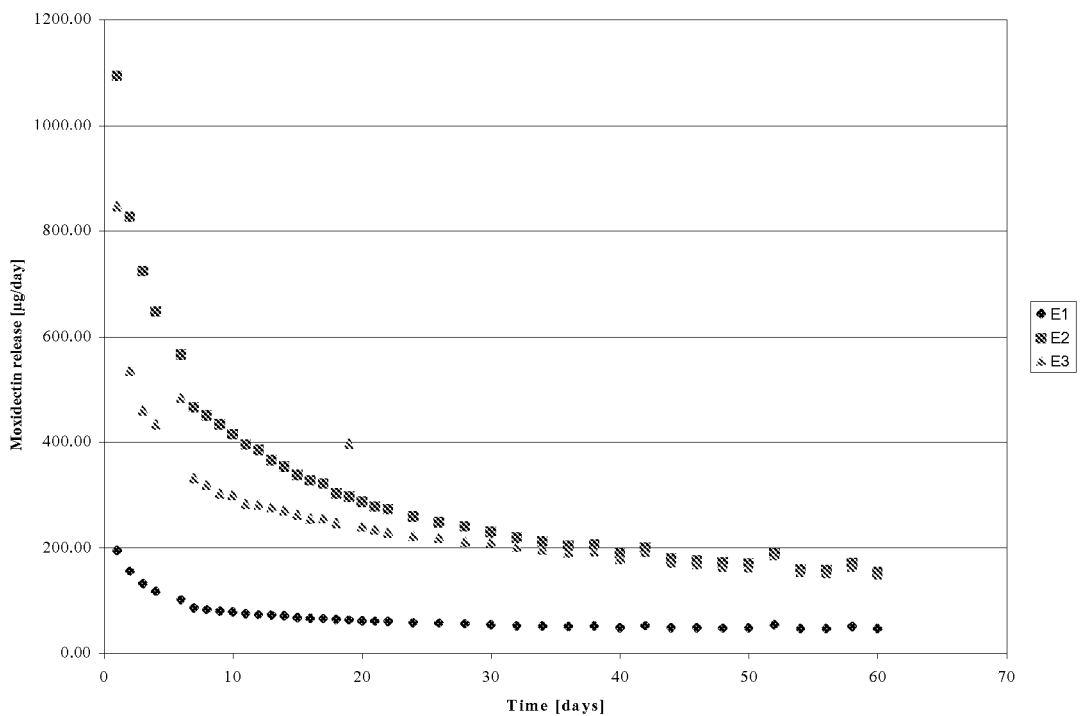
FIG. 6 shows the in vitro moxidectin release of implant designs of variant E
Figure 7:
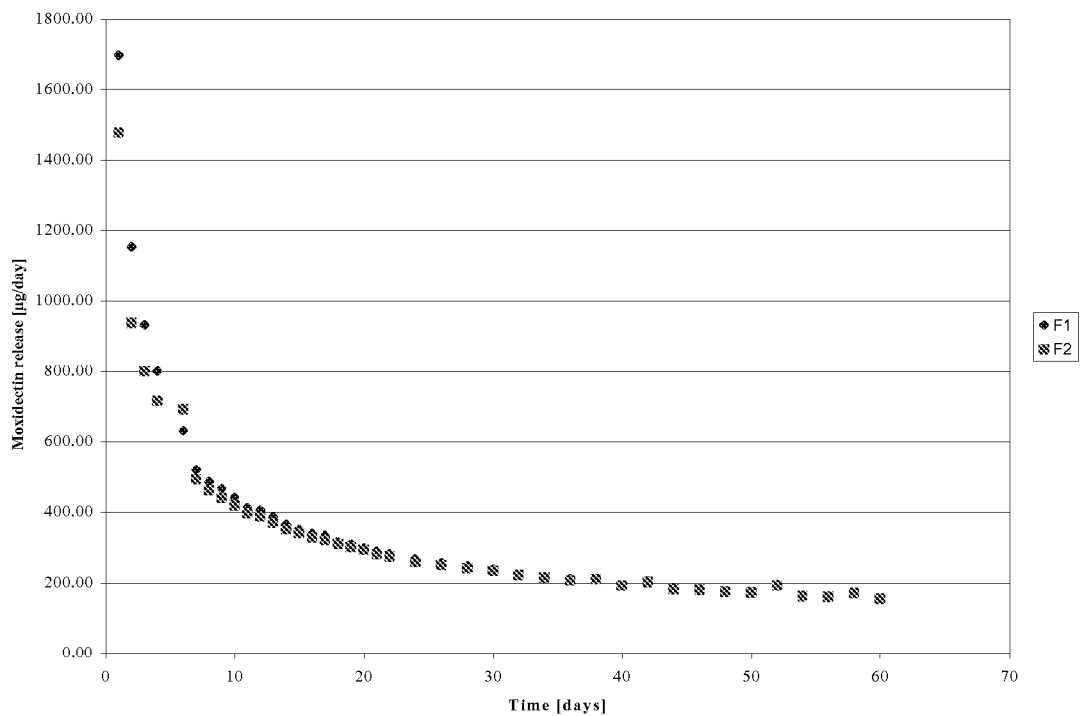
FIG. 7 shows the in vitro ivermectin release of implant designs of variant F
Figure 8:
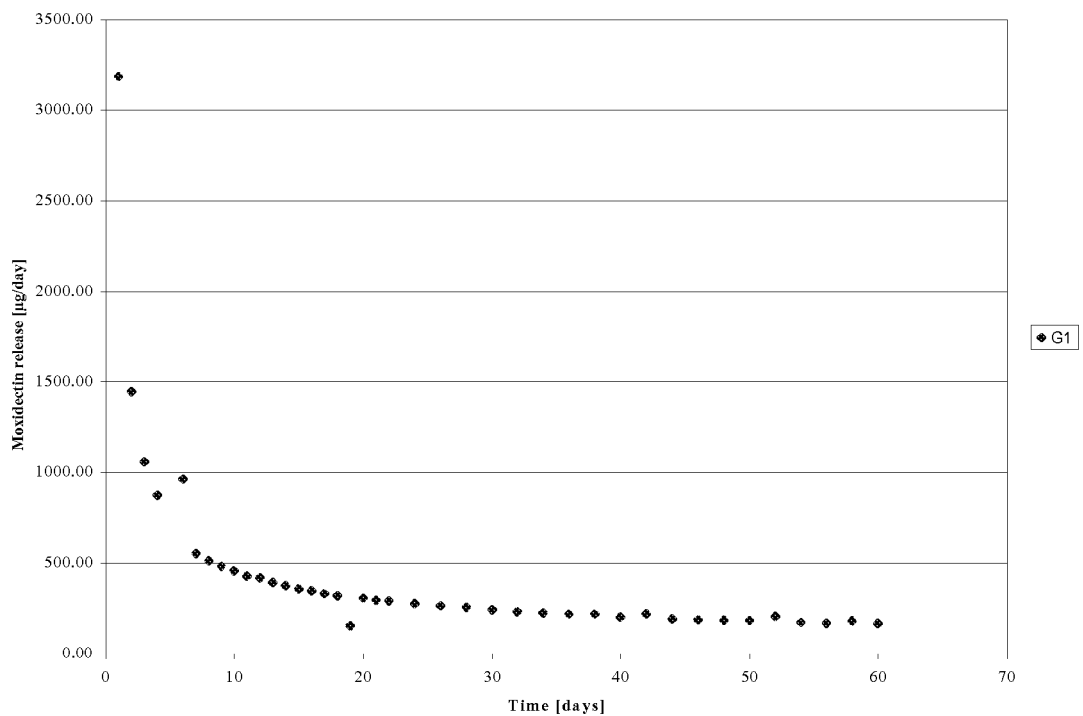
FIG. 8 shows the in vitro ivermectin release of implant designs of variant G

Results for in-vitro release for implants containing moxidectin are shown in Table 3B. FIG. 6 shows the in-vitro release profiles of implant designs of variant E. FIG. 7 shows the in-vitro release profiles of implant designs of variant F. FIG. 8 shows the in-vitro release profiles of implant designs of variant G.

TABLE 3B

In-vitro Moxidectin release rates in water/sodium lauryl sulphate (SLS) (0.9%).

| Variant | Ivermectin release day 1 [μg/day] | Ivermectin release day 2-60 [μg/day] | Ivermectin release day 60 [μg/day] |
|---|---|---|---|
| E1 | 195 | 66 | 46 |
| E2 | 1095 | 311 | 155 |
| E3 | 846 | 251 | 150 |
| F1 | 1698 | 339 | 157 |
| F2 | 1479 | 324 | 157 |
| G1 | 3185 | 363 | 166 |

Example II

Three implants, with different designs, were damaged by applying a cross sectional cut, introducing two new additional open fiber ends (Table 4). These damages were introduced to illustrate the robustness against dose dumping.

TABLE 4

Dimensions of damaged implants

| Variant | Original implant | Introduced damage |
|---|---|---|
| H1 | A1 | Cross sectional cut |
| H2 | A2 | Cross sectional cut |

Figure 9:
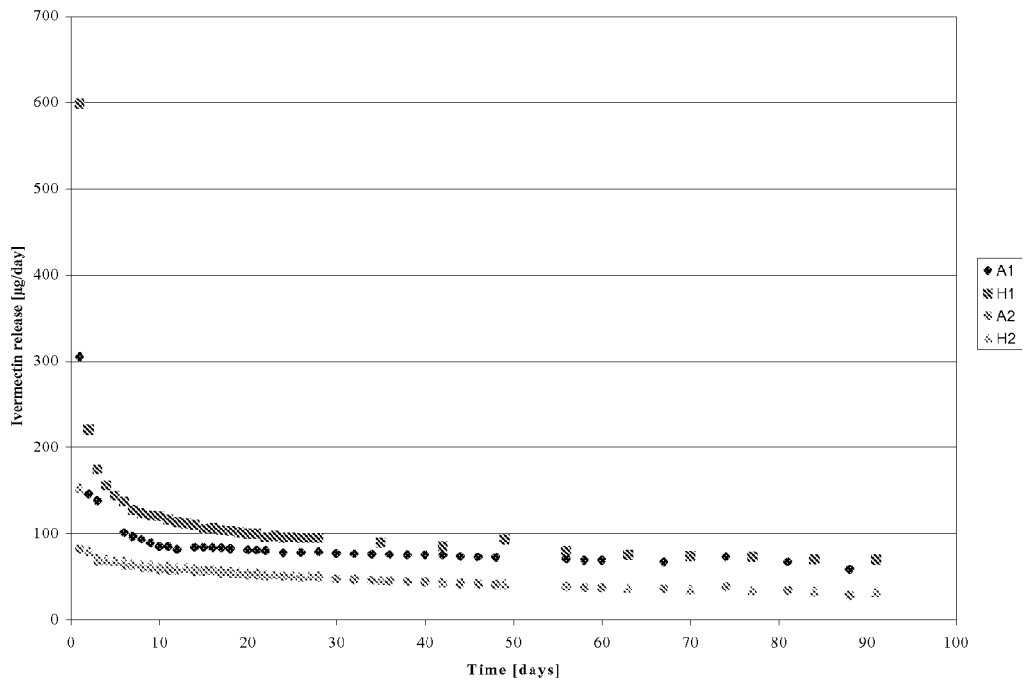
FIG. 9 shows the in vitro ivermectin release of implant designs of variant H (cross sectional cut)

Results for in-vitro release for damaged implants containing ivermectin are shown in Table 5. FIG. 9 shows the in-vitro release profiles of implant designs of variant H and A1.

TABLE 5

In-vitro Ivermectin release rates of damaged implants in water/sodium lauryl sulphate (SLS) (0.9%).

| Variant | Original implant | Ivermectin release day 1 [μg/day] | Ivermectin release day 2-91 [μg/day] | Ivermectin release day 91 [μg/day] |
|---|---|---|---|---|
| H1 | A1 | 153 | 49 | 32 |
| H2 | A2 | 600 | 99 | 70 |

Example III

Effect of Implant Length on In-Vitro Release Rate

TABLE 6A

In-vitro Ivermectin release rates of shortened implants in water/sodium lauryl sulphate (SLS) (0.9%).

| Variant | Original implant | Change to original implant |
|---|---|---|
| J1 | A1 | Shortened implant, i.e. 4 cm in length |

In order to made an implant batch useful for an in vivo dog study, the 6 cm implants of batch A1 were shortened to 4 cm resulting in batch J1

Figure 10:
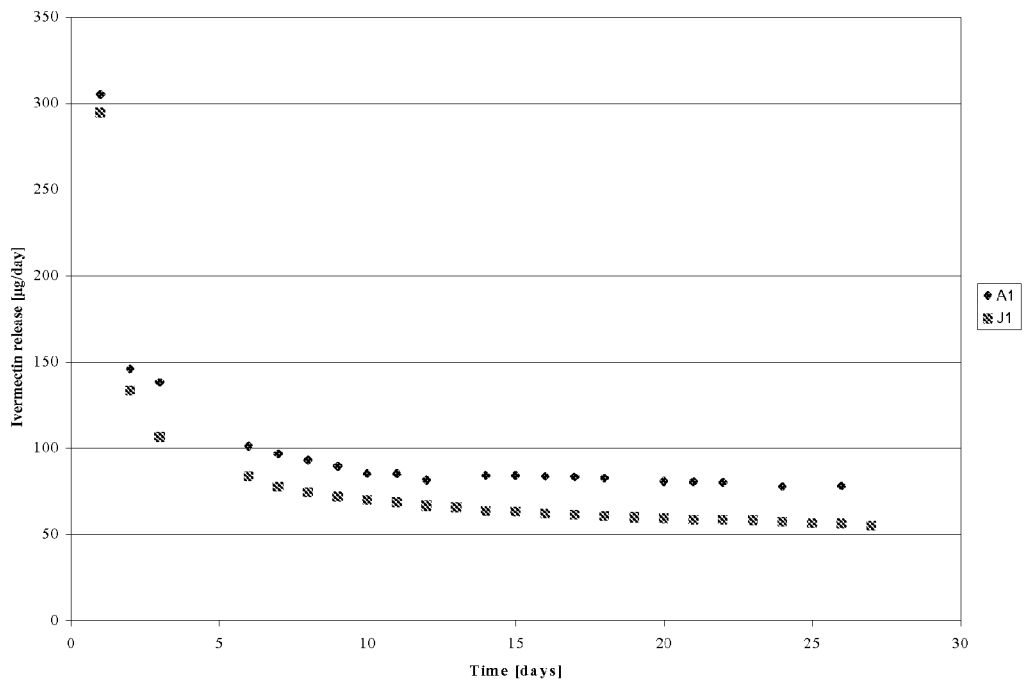
FIG. 10 shows the in vitro ivermectin release of implant designs of variant J (shortened implant)

Results for in vitro release for damaged implants containing ivermectin are shown in Table 6B. FIG. 10 shows the in-vitro release profiles of implant designs of variant J and A1.

TABLE 6B

In-vitro Ivermectin release rates of damaged implants in water/sodium lauryl sulphate (SLS) (0.9%).

| Variant | Original implant | Ivermectin release day 1 [µg/day] | Ivermectin release day 2-27 [µg/day] | Ivermectin release day 27 [µg/day] |
|---|---|---|---|---|
| J1 | A1 | 295 | 69 | 55 |

Example IV

Five batches, three ivermectin implants (A1, A2 and B1) and two moxidectin implants (E1, F2), were analyzed for long-term in-vitro release rates up to 333 days, see 7A and Table 7B.

TABLE 7A

In-vitro Ivermectin release rates of implants in water/sodium lauryl sulphate (SLS) (0.9%) for 333 days

| Variant | Ivermectin release day 1 [µg/day] | Ivermectin release day 2-333 [µg/day] | Ivermectin release day 333 [µg/day] |
|---|---|---|---|
| A1 | 305 | 67 | 51 |
| A2 | 47 | 35 | 16 |
| B1 | 551 | 175 | 138 |

TABLE 7B

In-vitro Moxidectin release rates of implants in water/sodium lauryl sulphate (SLS) (0.9%) for 316 days.

| Variant | Moxidectin release day 1 [µg/day] | Moxidectin release day 2-316 [µg/day] | Moxidectin release day 316 [µg/day] |
|---|---|---|---|
| E1 | 195 | 58 | 43 |
| F2 | 1479 | 248 | 76 |

Figure 11:
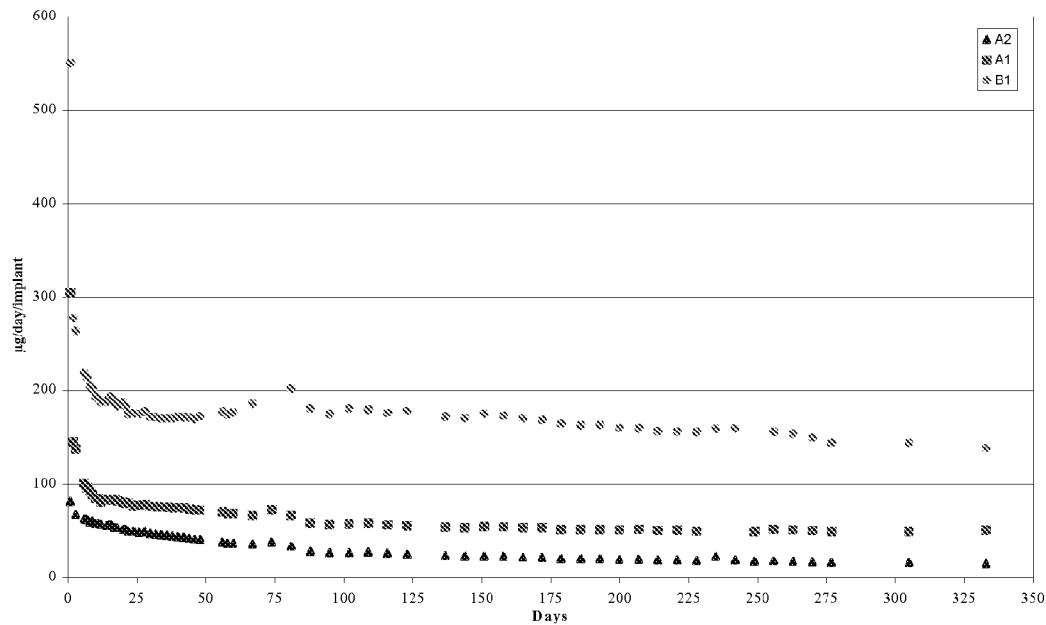
FIG. 11 shows the long term in vitro ivermectin release of implant designs of variant A1, A2 and B1 and J1 for 333 days.

FIG. 11 shows the in-vitro release profiles of implant designs of variants A1, A2, B1 until day 333.

Figure 12:
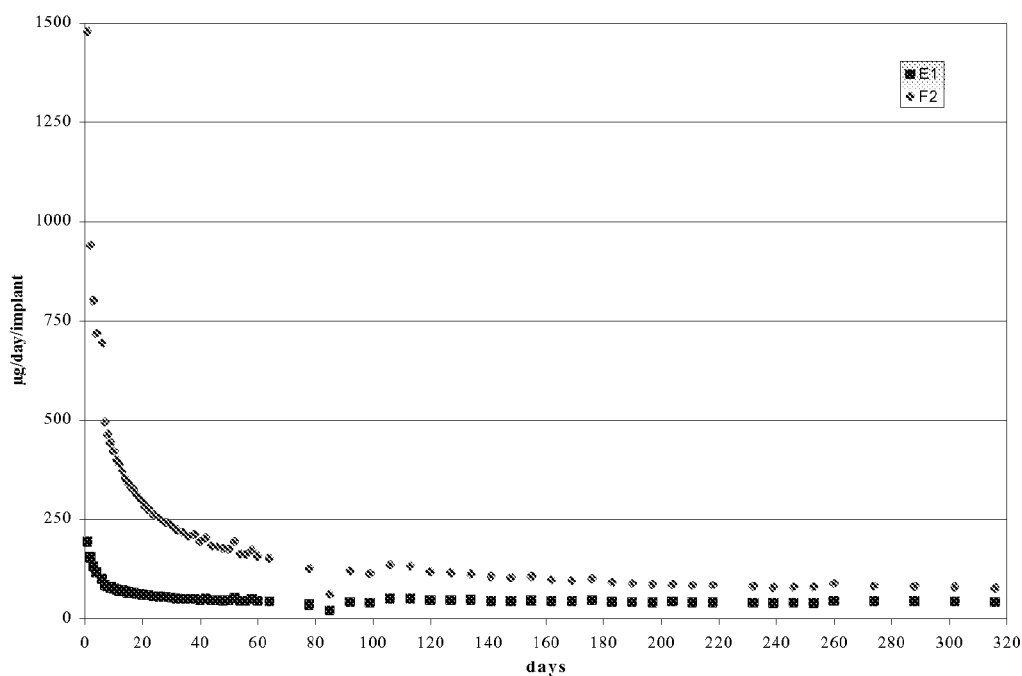
FIG. 12 shows the long term in vitro moxidectin release of implant designs of variant E1 and F2 for 333 days.

FIG. 12 shows the in-vitro release profiles of implant designs of variant E1 and F2.

Assessment of Release Kinetics

The in-vitro release kinetics of the batches A1, A2, B1, E1 and F2 were assessed by two independent methods.

In the first method, the semi-empirical equation of Peppas (Pharm. Acta Helv 60, Nr 4 (1985)) was applied on the in-vitro release data $$\frac{Mt}{M\infty} = k * t^n$$

With: $Mt/M\infty$=fractional release of the drug, k=constant, t=release time

If the value "n" approaches 1.0 this indicates a non-Fickian release mechanism (zero order release kinetics).

In the second method, the in-vitro release during the final 10% of the release period was divided by the average in-vitro release rate from day 15-323 for Moxidectin implants and day 10-333 for Ivermectin implants. If the ratio is 1.0, a perfect zero-order release kinetics is obtained.

Note: For the applied calculations, the first 9 days (for Ivermectin implants) and 14 days (for Moxidectin implants) of the release curve were omitted because a steady state release rate was achieved after approximately 9 or 14 days of release respectively.

The following results were found.

TABLE 8A

Release kinetics for Ivermectin implants

| Variant | n-value | Ratio release rate during last 10% of curve/average release day 10-333 |
|---|---|---|
| A1 | 0.8 | 0.9 |
| A2 | 0.6 | 0.6 |
| B1 | 0.9 | 0.9 |

TABLE 8B

Release kinetics for Moxidectin implants

| Variant | n-value | Ratio release rate during last 10% of curve/average release day 15-323 |
|---|---|---|
| E1 | 0.8 | 1.0 |
| F2 | 0.5 | 0.6 |

Some implants show almost perfect zero-order release kinetics (A1, B1 and E1). The release kinetics of the implant can be changed to a more matrix-type by either changing the concentration of the active compound in the core (compare A1 with A2) or by applying another skin polymer (E1 versus F2).

The data revealed that by changing the implant design, not only the absolute release rate (Table 7A and 7B) but also the release kinetics can be tailored as well.

Example V

Three batches ivermectin implants (A1, A2 and B1) were analyzed for long-term in-vitro release rates up to 609 days, see Table 9A

TABLE 9A

In-vitro Ivermectin release rates of implants in water/sodium lauryl sulphate (SLS) (0.9%) for 609 days.

| Variant | Ivermectin release day 1 [µg/day] | Ivermectin release day 2-609 [µg/day] | Ivermectin release day 609 [µg/day] |
|---|---|---|---|
| A1 | 391 | 54 | 49 |
| A2 | 131 | 20 | 11 |
| B1 | 672 | 132 | 62 |

Figure 13:
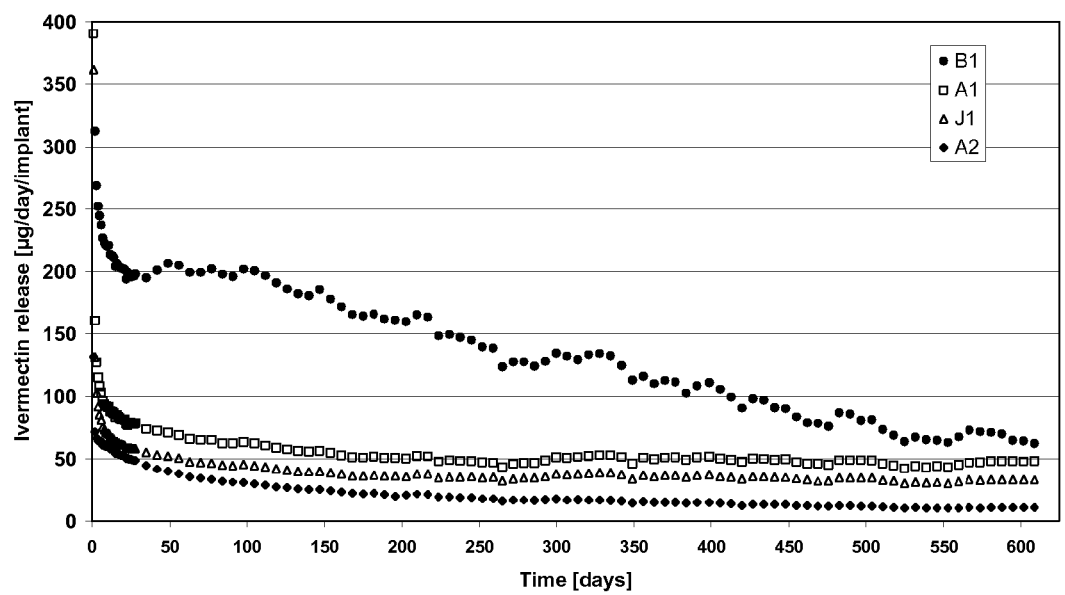
FIG. 13 shows the long term in vitro ivermectin release of implant designs of variant A1, A2 and B1 for 609 days.

FIG. 13 shows the in-vitro release profiles of implant designs of variants A1, A2, J1 B1 and J1 until day 609.

The in-vitro release kinetics of the batches A1, A2, and B1 were assessed by two independent methods.

In the first method, the semi-empirical equation of Peppas (Pharm. Acta Helv 60, Nr 4 (1985)) was applied on the in-vitro release data $$\frac{Mt}{M\infty} = k * t^n$$

With: Mt/M∞=fractional release of the drug, k=constant, t=release time

If the value "n" approaches 1.0 this indicates a non-Fickian release mechanism (zero order release kinetics).

In the second method, the in-vitro release during the final 10% of the release period was divided by the average in-vitro release rate from day 10-609. If the ratio is 1.0, a perfect zero-order release kinetics is obtained.

Note: For the applied calculations, the first 9 days of the release curve were omitted because a steady state release rate was achieved after approximately 9 or 14 days of release respectively.

The following results were found.

TABLE 9B

Release kinetics for Ivermectin implants

| Variant | n-value | Ratio release rate during last 10% of curve/average release day 10-609 |
|---|---|---|
| A1 | 0.8 | 0.9 |
| A2 | 0.6 | 0.5 |
| B1 | 0.7 | 0.5 |

Implant A1 shows almost perfect zero-order release kinetics.

Example VI

In Vivo Pharmacokinetic Profile in Dog Plasma after s.c. Implantation of an Ivermectin Loaded EVA Implant Composition of the ivermectin loaded EVA implant: (84 mg ivermectin/implant)
Core: 46.9% EVA 28
  50% Ivermectin
  3% BaSO$_4$
  0.1% Magnesium stearate
Skin: EVA 28 thickness 90 µm.
Implant thickness: 2.5 mm.
Length: approximately 4 cm.

Material and Methods: 6 healthy Beagle dogs were weighed and included in the study. On D0 one ivermectin implant (84 mg ivermectin/implant) per dog was subcutaneously administered in the umbilical region. On D1 and D2 implant location was examined twice daily and thereafter at each blood sampling time point. At the same time points all dogs were physically examined by a veterinarian.

Blood samples were taken pre-administration (D-3) and on D2, D3, D4, D7, D14, D28 and subsequently every four weeks until D532.

The plasma was analyzed for ivermectin concentrations, utilizing an analytical HPLC procedure with a lower limit of quantification of approximately 0.25 ng/mL.

The following pharmacokinetic parameters were determined for each animal for the concentrations [ng/mL] of ivermectin in dog plasma: observed $C_{max}$[ng/mL], observed $T_{max}$[d] and $AUC_{last}$[ng/mL*d].

$AUC_{last}$ was calculated using the linear trapezoidal rule from time 0 to the last quantifiable data point:

$$AUC = \frac{1}{2} \cdot \sum_{i=1}^{n-1} (t_{i+1} - t_i) \cdot (c_i + c_{i+1}) = \frac{1}{2}\left(c_n t_n - c_1 t_1 + \sum_{i=1}^{n-1} c_i t_{i+1} - \sum_{i=1}^{n-1} c_{i+1} t_i\right)$$

where $t_i$ is the $i^{th}$ time point and
ci is the plasma concentration at the $i^{th}$ time point.

At the end of the study, all implants were removed, as well as adherent connective tissue and the remaining ivermectin content was analyzed.

Results:

Insertion of ivermectin implants on D0 proceeded in all animals without abnormalities. Except a slight redness and swelling of implantation site on D1 and D2 in some dogs, nothing irregular was detected throughout the whole study. In 5 of 6 dogs no movements of the implant were observed. In one dog the implant was a bit displaced to the left side, but without any influence on ivermectin pharmacokinetics or wellbeing of the dog.

The mean ivermectin plasma concentration increased from 1.53±0.28 ng ivermectin/mL plasma (D1) up to 3.57±0.87 ng ivermectin/mL plasma (D3) and decreased from then on to 0.25±0.29 ng ivermectin/mL plasma (D505). On D532, mean ivermectin plasma concentration was below limit of quantification (LOQ).

Mean $C_{max}$ (3.70±0.83 ng ivermectin/mL) was observed after 5.0±2.2 d (mean observed $T_{max}$) and mean $AUC_{last}$ was 539±168 d*ng/mL.

The time course of the mean ivermectin plasma concentration is shown in FIGS. 14 and 15.

CONCLUSION

Ivermectin EVA implants had no influence on health and wellbeing of the animals and showed no clinical adverse effects. Ivermectin plasma concentrations over the limit of quantification were measured in all dogs up to 1 year and in 3 of 4 dogs up to 15 months.

The invention claimed is:
1. A drug delivery system for the controlled release of a macrocyclic lactone as an active ingredient, consisting of a solid non-porous reservoir made of a pharmaceutically acceptable polyethylene vinyl acetate copolymer, loaded with the macrocyclic lactone, magnesium stearate and a non-porous skin covering the reservoir, the skin comprising a polyethylene vinyl acetate copolymer wherein the macrocyclic lactone is released substantially by diffusion through the skin of the drug delivery system, and wherein the drug delivery system is in the form of a subcutaneous implant capable of delivering an effective dose of the macrocyclic lactone for a period of 1 to 3 years.

2. A drug delivery system according to claim 1, wherein the polyethylene vinyl acetate copolymer used in the reservoir comprises of from 25 to 35% by weight of vinyl acetate.

3. A drug delivery system according to claim 1, wherein the polyethylene vinyl acetate copolymer used in the skin comprises of from 7%-35% by weight of vinyl acetate.

4. The drug delivery system according to claim 3, wherein the polyethylene vinyl acetate copolymer used in the skin comprises of from 15 to 30% by weight of vinyl acetate.

5. A drug delivery system according to claim 1, wherein the reservoir and the skin comprise the same polyethylene vinyl acetate copolymer.

6. A drug delivery system according to claim 5, wherein the polyethylene vinyl acetate copolymer has a vinyl acetate content of 28% by weight.

7. A drug delivery system according to claim 1, in the form of a cylindrical rod wherein the reservoir and the skin layer are concentric with the axis of the rod.

8. A drug delivery system according to claim 1, wherein the macrocyclic lactone is selected from the group consisting of ivermectin, moxidectin, selamectin, doramectin, abamectin, and mixtures thereof.

9. A drug delivery system according to claim 1, obtainable by a method in which a thermoplastic polymer solid reservoir loaded with the macrocyclic lactone at a concentration above the saturation concentration at 25° C., is co-extruded with a thermoplastic polymer not loaded with the macrocyclic lactone, and the resulting co-extrudate is cut, wherein the direction of cutting is substantially different from the direction of extruding.

10. The drug delivery system according to claim 9, wherein the thermoplastic polymer is a polyethylene vinyl acetate copolymer.

11. The drug delivery system according to claim 9, wherein the direction of cutting is perpendicular to the direction of extruding.

12. A drug delivery system for the controlled release of a macrocyclic lactone as an active ingredient consisting of a solid non-porous reservoir made of a pharmaceutically acceptable polyethylene vinyl acetate copolymer loaded with the macrocyclic lactone, magnesium stearate, a radiocontrast agent and a non-porous skin covering the reservoir, the skin comprising a polyethylene vinyl acetate copolymer wherein the macrocyclic lactone is released substantially by diffusion through the skin of the drug delivery system, and wherein the drug delivery system is in the form of a subcutaneous implant capable of delivering an effective dose of the macrocyclic lactone for a period of 1 to 3 years.

13. The drug delivery system of claim 12, wherein the radiocontrast agent is barium sulphate.

14. A method of treating parasitic diseases in animals, which method includes administering to an animal the drug delivery system according to claim 1 comprising an antiparasitically effective amount of a macrocyclic lactone.

15. The method of claim 14, wherein the animal is selected from the group of canines, felines, rodents, horses, and cattle.

16. The method according to claim 14, wherein the parasitic disease is a heartworm infection in canines or felines.

* * * * *